United States Patent
Glaser et al.

(10) Patent No.: US 7,709,241 B2
(45) Date of Patent: May 4, 2010

(54) METHOD OF MAKING MICROORGANISM SAMPLING TUBE CONTAINING SLANTED CULTURE MEDIUM AND SAMPLE TUBE TRAY THEREFOR

(75) Inventors: Mark Glaser, Crownsville, MD (US); Charles Muller, Glen Rock, PA (US); Angelo Cordero, San Jose, CA (US); Kim Torppey, Baltimore, MD (US); David Racine, Whiteford, MD (US); Roy Henderson, Westminster, MD (US); Gregorio Aragon, Joppa, MD (US); Michael Zabetakis, Hampstead, MD (US); Carter S. Dowlin, Westminister, MD (US); Chandra Schaub, Nottingham, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 904 days.

(21) Appl. No.: 11/079,909

(22) Filed: Mar. 15, 2005

(65) Prior Publication Data
US 2005/0214924 A1    Sep. 29, 2005

Related U.S. Application Data

(60) Provisional application No. 60/553,536, filed on Mar. 17, 2004, provisional application No. 60/553,537, filed on Mar. 17, 2004.

(51) Int. Cl.
    *C12N 1/12*    (2006.01)
(52) U.S. Cl. .................. 435/252.1; 435/253.6
(58) Field of Classification Search ............. 435/296.1, 435/299.1, 304.1, 809, 252.1, 253.6
See application file for complete search history.

(56) References Cited

U.S. PATENT DOCUMENTS 2,902,170 A    9/1959    Miller (Continued)

FOREIGN PATENT DOCUMENTS

JP    2002-098704    *    5/2002

OTHER PUBLICATIONS

Getinge Brochure, A Commitment to Lead, Advancing Pharmaceutical Processing, Getinge Scientific (Date unknown).

(Continued)

*Primary Examiner*—Michael A Marcheschi
*Assistant Examiner*—Michael Hobbs
(74) *Attorney, Agent, or Firm*—Lerner, David, Littenberg, Krumholz & Mentlik, LLP

(57) ABSTRACT

A method of making sampling tubes containing culture growth media by loading the sample tubes containing culture media into a tray that holds the sample tubes, placing the sample tube trays into a rack with shelving to hold the trays and tubes at a predetermined angle, and sterilizing and cooling the sample tubes in an autoclave or inspissator. The culture growth media solidifies at the predetermined slant angle and the sample tube trays are loaded into the packaging box used for shipment. The trays are subsequently used by the end user for processing microbial growth, including storing and collecting data about microbial samples.

19 Claims, 16 Drawing Sheets

U.S. PATENT DOCUMENTS

| | | | |
|---|---|---|---|
| 3,935,067 A * | 1/1976 | Thayer | 435/397 |
| D246,466 S | 11/1977 | Attree | |
| 4,060,457 A * | 11/1977 | Iizuka et al. | 435/283.1 |
| 4,407,958 A | 10/1983 | DeGraff, Jr. | |
| 4,932,533 A * | 6/1990 | Collier | 206/569 |
| 5,080,232 A | 1/1992 | Leoncavallo et al. | |
| 5,133,939 A | 7/1992 | Mahe | |
| 5,285,907 A | 2/1994 | Franchere et al. | |
| 5,415,846 A | 5/1995 | Berry, Jr. | |
| 5,489,532 A * | 2/1996 | Charm et al. | 435/286.1 |
| 5,632,388 A * | 5/1997 | Morrison et al. | 211/74 |
| 5,993,745 A | 11/1999 | Laska | |
| 6,123,205 A * | 9/2000 | Dumitrescu et al. | 211/74 |
| 6,127,138 A * | 10/2000 | Ishimaru et al. | 435/23 |
| 6,164,044 A | 12/2000 | Porfano et al. | |
| 6,189,292 B1 | 2/2001 | Odell et al. | |
| 6,250,052 B1 | 6/2001 | Porfano et al. | |
| 6,479,116 B1 * | 11/2002 | Small et al. | 428/36.7 |
| D533,948 S * | 12/2006 | Schaub et al. | D24/229 |
| 2002/0090320 A1 * | 7/2002 | Burow et al. | 422/64 |
| 2002/0108917 A1 | 8/2002 | Maruyama | |
| 2004/0023374 A1 * | 2/2004 | Rappaport et al. | 435/325 |

OTHER PUBLICATIONS

Drawing Entitled Test Tube Tray, Aug. 2, 2001.
Drawing Entitled Test Tube Tray-Conceptual, Sep. 27, 2000.

* cited by examiner

METHOD OF MAKING MICROORGANISM SAMPLING TUBE CONTAINING SLANTED CULTURE MEDIUM AND SAMPLE TUBE TRAY THEREFOR

CROSS-REFERENCE TO RELATED APPLICATIONS

This application claims the benefit under 35 U.S.C. §119(e) of U.S. Provisional Patent Application Ser. Nos. 60/553,536 and 60/553,537, both of which were filed on Mar. 17, 2004 in the U.S. Patent and Trademark Office, the entire contents of each said application being hereby incorporated by reference.

FIELD OF THE INVENTION

The present invention relates generally to a method of making microorganism sampling tubes containing slanted culture media utilizing an autoclaveable tray that can be used throughout the production process from filling, capping, and labeling of the sampling tubes to sterilizing and cooling the sampling tubes and culture medium in a slanted position and then packaging the sampling tubes for shipment.

BACKGROUND OF THE INVENTION

When autoclaving sample tubes containing growth media, the current state of the art is to use a number of different trays to achieve the final result. In some cases, up to three different trays are used to produce a sample tube with slanted growth media. Since the autoclave is a high heat and pressure device, the tray must be capable of withstanding both high heat and high pressure. Typically, a metal tray is used in autoclaves because of its tolerance to high temperature and overall ruggedness when being handled. However, the metal tray has several disadvantages, including longer heating and cooling cycles, imprecision of fit for the sample tubes within the holes of the tray, limited size, and weight. These last two disadvantages are critical because the heavier weight limits the size of the tray, which in turn limits the throughput of a labor intensive production line and, if used to ship the sample tubes, increases shipping costs. To compensate for these disadvantages, a manufacturer must perform all of the production steps other than autoclaving using a lighter weight tray with a greater tube capacity than the metal tray. But by adding another tray to the process, additional steps of removing the tubes from one tray (called detraying) and placing the tubes in metal trays for autoclaving become necessary. The tubes must then be detrayed again for placement into shipping trays, which may or may not be the same trays used for handling prior to autoclaving. Improvements are therefore desired.

The prior art sample tube shipping or packaging trays 70, as shown in FIG. 4, do not have well bottoms that support the sample tubes 150 from beneath. This creates potential problems when filled trays 70 are stacked one on top of another or when the filled trays 70 are placed on an uneven surface. The tray 70 does not have a means for securely holding the sample tubes 150 even when the trays are upright. This loose fit is problematic because the sample tubes 150 may be damaged. The trays 70 merely have a well opening 80 large enough to accommodate sample tubes 150 and the sample tubes 150 have a height taller than the legs 82 of the trays 70. Since the sample tubes 150 are taller than the trays and the well openings 80 are loose, picking up the trays 70 to move them causes the sample tubes 75 to slide down in the well openings 80 up to their caps 72. In addition, when the trays 70 are placed on an uneven surface, the sample tubes 150 may slide upwardly in the well opening or down to conform to the uneven surface. The loose fit of the sample tubes 150 in the tray 70 make the tray unsuitable for producing slanted growth media in an autoclave or inspissator. Completely enclosing the sample tubes 150 insulates the sample tube from the sterilizing steam and the cooling air/water of the autoclave cycle possibly resulting in incomplete sterilization, as well as inhibiting cooling.

SUMMARY OF THE INVENTION

The present invention is directed to an autoclaveable tray that can be used throughout the manufacturing process and with a variety of culture growth media, including broths, agars and slant agars. More specifically, the invention is directed to a plastic tray with a number of wells for holding tubes with each well comprising a plurality of legs, a support rib extending downwardly along the inside of each leg to firmly hold the sample tube in place, and a bottom with a hole. The opening of the well is preferably larger in diameter than the bottom of the well. The tray may further comprise a flange around the perimeter of the tray. Finally, the tray preferably comprises alternating rows of even and odd numbers of wells in a rectangular array. The trays can firmly hold sample tubes filled with culture growth media, both broths and agars, in either a horizontal configuration or a slanted configuration, while the tubes are placed in a sterilization device, such as an autoclave or an inspissator.

The present invention is also directed to a method for making microorganism sampling tubes containing slanted culture growth media utilizing the autoclaveable tray and subsequent use of the tray by the end user. More specifically, the invention is directed a method of making a sample tubes containing slanted culture growth media. The method begins with the steps of filling the sample tubes with non-sterile culture media and loading a plurality of tubes filled with culture media into at least one packaging tray. The packaging tray is placed onto a rack, the rack maintaining the packaging tray in a position that slants the culture media at a predetermined slant angle within the tubes. An autoclave sterilizes the rack and packaging tray holding the tubes filled with culture growth media. The autoclave process includes a sterilization (heating) cycle as well as a cooling cycle, the two cycles together being referred to hereinafter as the autoclave cycle. The tubes are cooled and packaged in the tray holding the tubes filled with culture media and the rack after completion of the sterilizing step within the autoclave so that the culture media solidifies within the tubes at the required slant angle. Finally, the packaging tray is loaded into shipping packages for shipment and subsequent use of the tray by the end user.

Accordingly, an object of the invention is to provide a single tray that can be used from the beginning of a culture growth media manufacturing process, including production of broth, agar and slant agar products, through the delivery at an end user site, where the single packaging tray may also be used by the end user to perform a variety of laboratory tasks corresponding to the growing cultures in the sample tubes and the subsequent examination of the cultures.

Another object of the invention is to provide a tray capable of being autoclaved and cooled while firmly holding sample tubes filled with agar, in particular, slant agar, thereby keeping the tubes and holding the tubes so that the slant and butt measurements are substantially uniform and within manufacturing tolerances.

Another object of the invention is to provide a tray capable of being robotically loaded with sample tubes.

Another object of the invention is to provide protection for the sample tubes by having a well bottom held securely in place by legs, thereby preventing the sample tubes from moving or becoming dislodged when trays filled with sample tubes are stacked one on top of another.

Another object of the invention is to provide the tray with a peripheral flange which prevents the trays from "shingling" or sliding over one another when placed side by side in the autoclave or anytime during the manufacturing process.

Another object of the invention is to provide a tray that facilitates use with standard shipping pallets. Additionally, the tapered legs of the sample tube wells allow empty trays to nest neatly one inside another.

Another further object of the invention is to provide an open tray well to expose the sides of the sample tubes for autoclaving. The open tray wells also allow liquids and gases to flow more freely around the sample tubes while being sterilized and cooled.

Another object of the invention is to provide a tray that may be used by the end user after shipment as a tube stand for use in the laboratory, or as a tube rack in an incubator, water bath, boiler or refrigerator.

Accordingly, a primary object of the present method is to provide a method for consistently producing slant agar products that meet the slant and butt measurement requirements.

Another object of the invention is to provide a method that allows for streamlined production operations by using the same sample tube tray throughout the production cycle. The method allows the same tray to be used for filling, capping, labeling, autoclaving, cooling and shipping.

Another object of the invention is to provide a sample tube tray that facilitates the streamlined manufacturing of a sample tube with a growth media culture. The sample tube tray comprises a plurality of sample tube wells for receiving sample tubes and holding sample tubes in place while moving along an assembly line, a flange to prevent said sample tube tray from sliding over the flange of another said sample tube tray when the sample tube trays are placed adjacent to one another, a minimum amount of surface area to remain structurally stable when fully filled with sample tubes and sterilized in a sterilization device and allow for substantially uniform sterilization and cooling of the sample tubes, a flat bottom for allowing said sample tube tray to remain stable when placed on uneven surfaces; and length and width dimensions that allow the sample tube tray filled with sample tubes to be placed into a shipping container.

Another object of the present invention is to provide a method for maintaining the tubes at the proper slant angle while the tubes are sterilized and cooled in an autoclave or inspissator.

Another object of the present invention is to provide a method of utilizing a slant rack design for the production of slanted agar products.

These and other aspects, advantages and salient features of the invention will become apparent to one skilled in the art from the attached drawings and the following detailed description which discloses preferred embodiments of the invention.

BRIEF DESCRIPTION OF THE DRAWINGS

The invention will be more readily understood with reference to the embodiments thereof illustrated in the attached drawing figures, which are described briefly below.

Throughout the drawing figures, it should be understood that like reference numerals refer to like features and structures.

DETAILED DESCRIPTION

Using an autoclaveable plastic tray that is capable of holding many sample tubes and is light in weight allows for more efficient handling of the trays by the production line workers. However, existing autoclaveable plastic trays are not capable of being used throughout the entire production process, particularly when slant media sample tubes are being manufactured. In the existing plastic trays, the sample tubes fit loosely in the holes in the tray. In addition, since the sample tubes are not firmly held by the tray and are exposed at the bottom, the sample tubes may be pushed up from underneath the tray and possibly out of the tray. Furthermore, if the tray is turned on its side, the sample tubes can easily fall out of the tray. Presently, there is not a tray capable of firmly holding sample tubes with growth culture media, both broth and slant agar, that can also be used in autoclaving and packaging. In particular, there exists a need for a tray capable of holding sample tubes at a slant as the tray and sample tubes are sterilized and cooled. It would be even more advantageous if the same tray could be used for shipping the finished sample tubes to the customer and for the customer to subsequently use at their facilities.

Slant agar products are used in a variety of biological tests. Testing is performed on both the slanted surface of the agar and below the surface of the agar; therefore, it is critical that the depth of the agar and the surface area be sufficient to insure proper growth conditions for the organism under test. Sample tubes of different sizes are used for different testing purposes.

Figure 1:
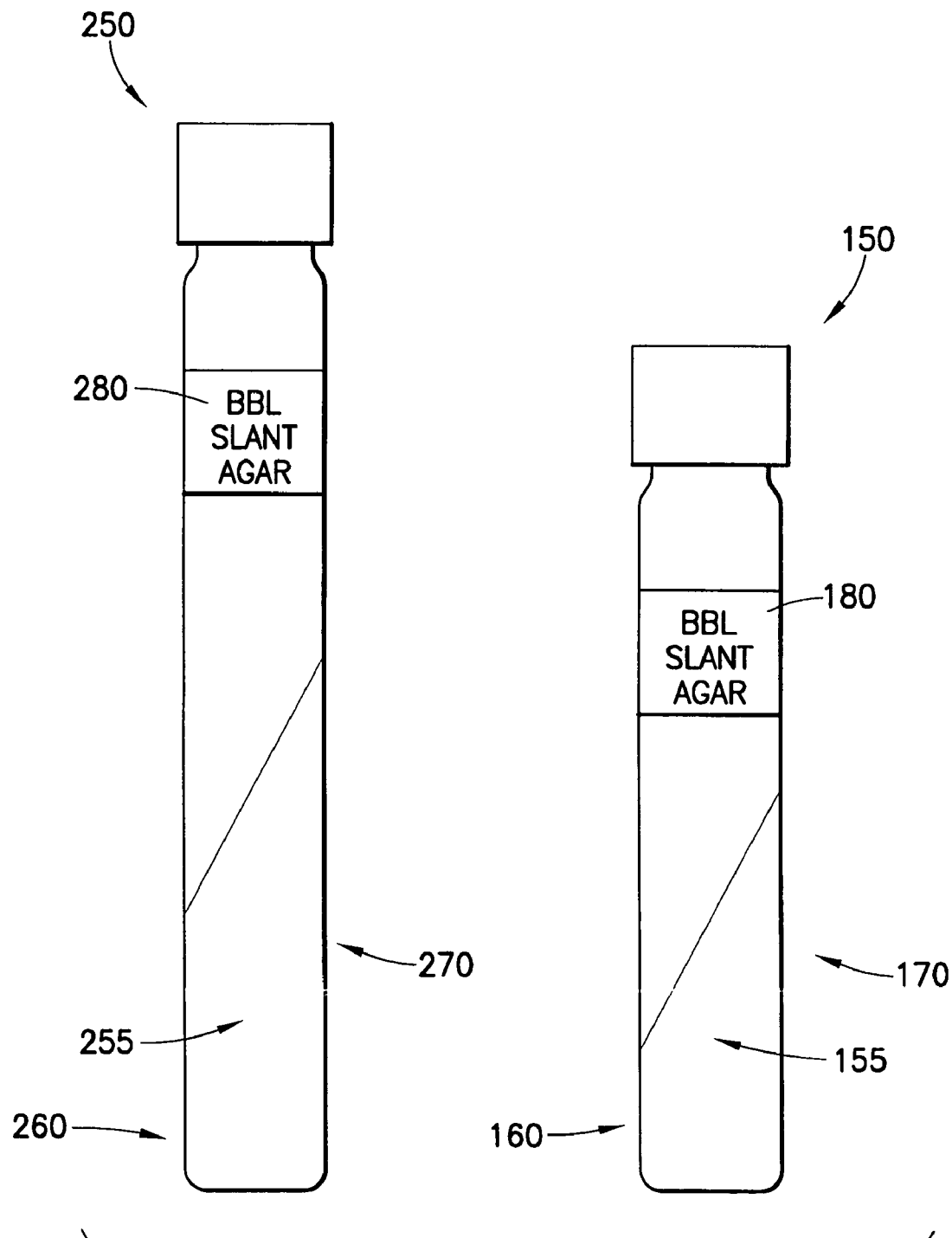
FIG. 1 shows exemplary sampling tubes containing slanted agar.

The prior art sample tubes of FIG. 1 have diameters of 16 mm (150) and 19 mm (250), respectively. Each tube requires a tray specifically designed for its diameter. The 16 mm tubes and 19 mm tubes (150) have different heights, but that does not affect the design of the tray. The tubes (150, 250) are shown with solid slant agar (155, 255, respectively). For certain culture growth media, the amount of slant (170, 270) and the height of the agar (160, 260) from the bottom of the tube, called the butt, are critical. The slant (170, 270) and butt (160, 260) measurements must be within certain tolerances to be acceptable for distribution. Sample tubes (150, 250) are labeled (180, 280) after sterilization in the prior art process and may be labeled before sterilization in the process of the present invention. A way of maintaining these critical measurements is to securely hold the sample tubes in the tray and to use a slant rack to insure that the trays are held at the proper slant angle throughout the sterilization and cooling phases, while the agar (155, 255) solidifies. The angle of the slant and butt measurement is determined by the fill height of the agar (155, 255) within the tube and the angle of the tray and tubes within the slant rack when the agar is cooling after it has been sterilized. FIG. 1 shows examples of two different sample tubes (150, 250) that can be made by the conventional processes as well as by embodiments of the present invention. However, embodiments of the present invention are not limited to only these tube sizes or slant agar growth culture media, as the trays and slant racks may be designed to accommodate any sample tube size and growth culture media as desired by the user.

Figure 2:
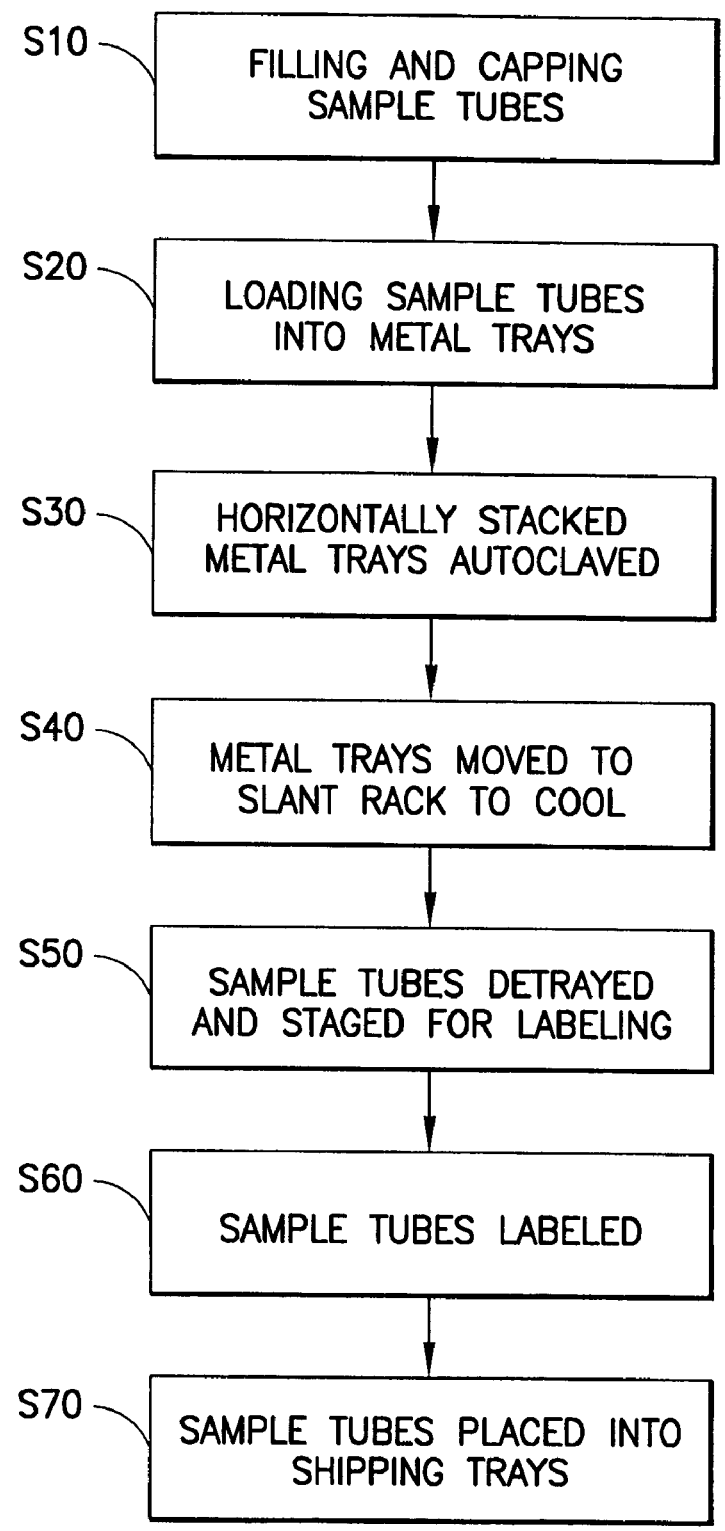
FIG. 2 is a flowchart of the conventional process steps for producing sampling tubes with sterilized slanted agar.

The prior art slant agar production process is shown in the flow chart of FIG. 2. Presently the sample tubes must be filled with previously prepared agar and capped (S10). The caps must be tightened to a predetermined torque requirement. After capping, the tubes are manually loaded (S20) into metal trays in preparation for sterilization. The metal trays are then stacked horizontally one on top of another before being placed in the autoclave (S30). The autoclave has two different cycles depending upon the product being manufactured, specifically, a time and temperature cycle or an $F_o$ cycle, which sterilizes the tubes and destroys any organisms in the agar. To make the slant products, the metal trays with the sterile sample tubes must be transferred from the autoclave to slant racks (S40) where the tubes are allowed to cool and the agar solidifies at the desired butt and slant measurements. After the sample tubes have cooled, the sample tubes must now be manually detrayed and staged for labeling (S50). After the sample tubes have been labeled (S60), the sample tubes are manually packed into plastic shipping trays (S70). All of these manual handling steps can damage the product, as well as slowing production and resulting in increased labor in an already labor intensive process.

Figure 3:
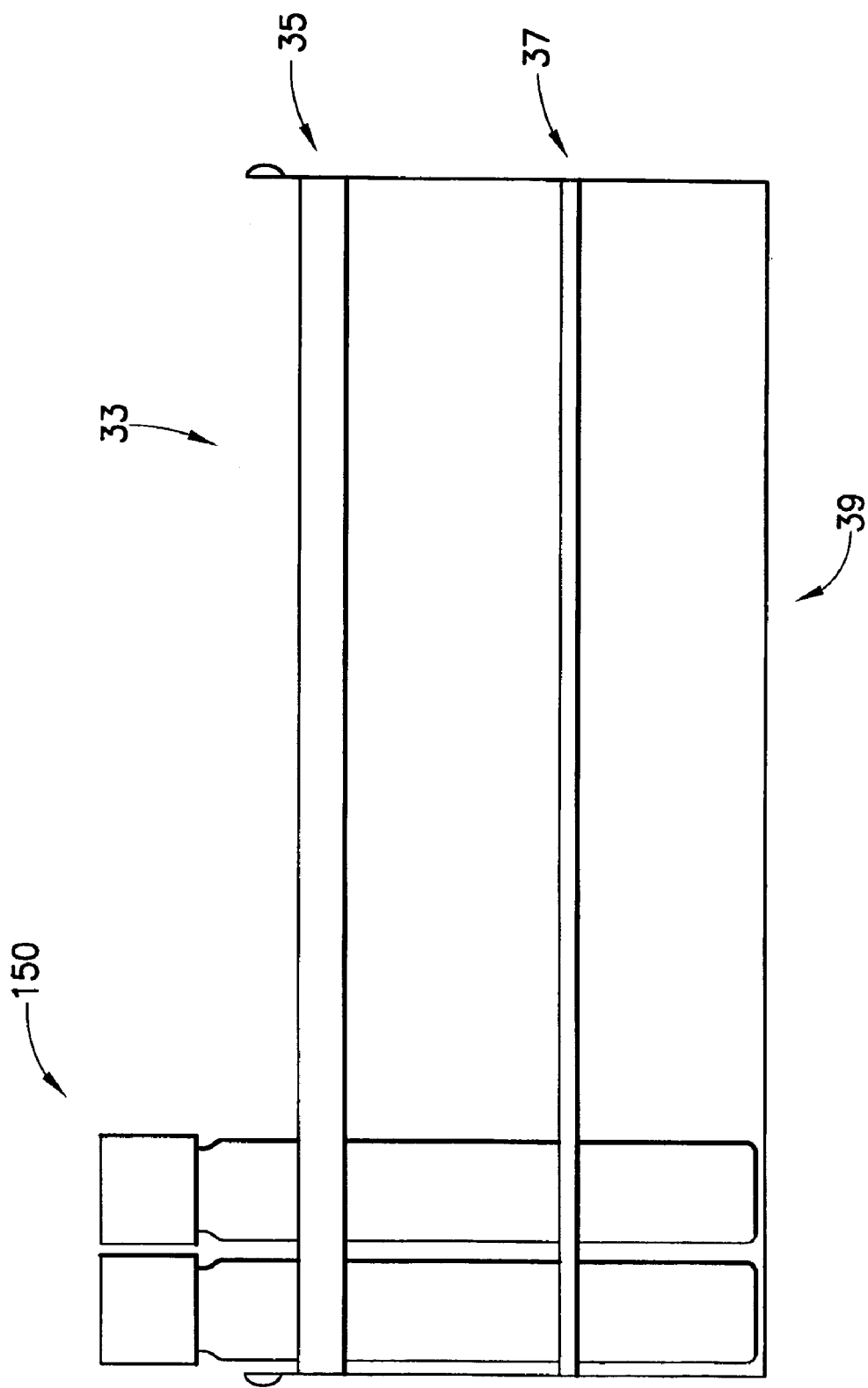
FIG. 3 illustrates the manner in which the exemplary sample tubes are placed in the conventional metal autoclave tray.

With reference to FIG. 3, the sample tubes 150 do not fit securely in the metal autoclave trays 33. When stacked horizontally this does not present much of a problem, but when producing slant agars the loose fit becomes problematic. Since the metal trays 33 do not firmly hold the sample tubes, the sample tubes may slide out or not stay completely in the tray when the trays are placed onto a slant rack. Only two shelves (35, 37) maintain the sample tubes 150 in the metal tray 33. The wells of the metal tray (not shown) have no means of frictionally holding the sample tubes 150. If the sample tubes 150 slide out of the metal tray 33, they may break or, even if they remain intact, they may not have the proper slant and butt measurements. If the sample tubes 150 do not remain completely in the metal tray 33, the slant and butt measurements will not meet requirements. Although, the metal autoclave tray 33 is shown containing the 16 mm sample tubes 150, the tray 33 is also used with the 19 mm sample tube trays 250. Even if the sample tubes 150 are in the proper position within the metal tray 33, the metal trays may themselves become misaligned in the slant rack, causing the slant and butt measurements to be out of specification. Another problem with the metal trays is that they are designed to be reused. Metal trays that are damaged (e.g., dented or twisted) may be reused many times, potentially creating a large number of products that do not meet specifications. In addition, the metal trays have solid bottoms (FIG. 3, element 39) which inhibit drainage of liquids and obstruct the flow of gases from the tray and around the sample tubes.

Figure 5:
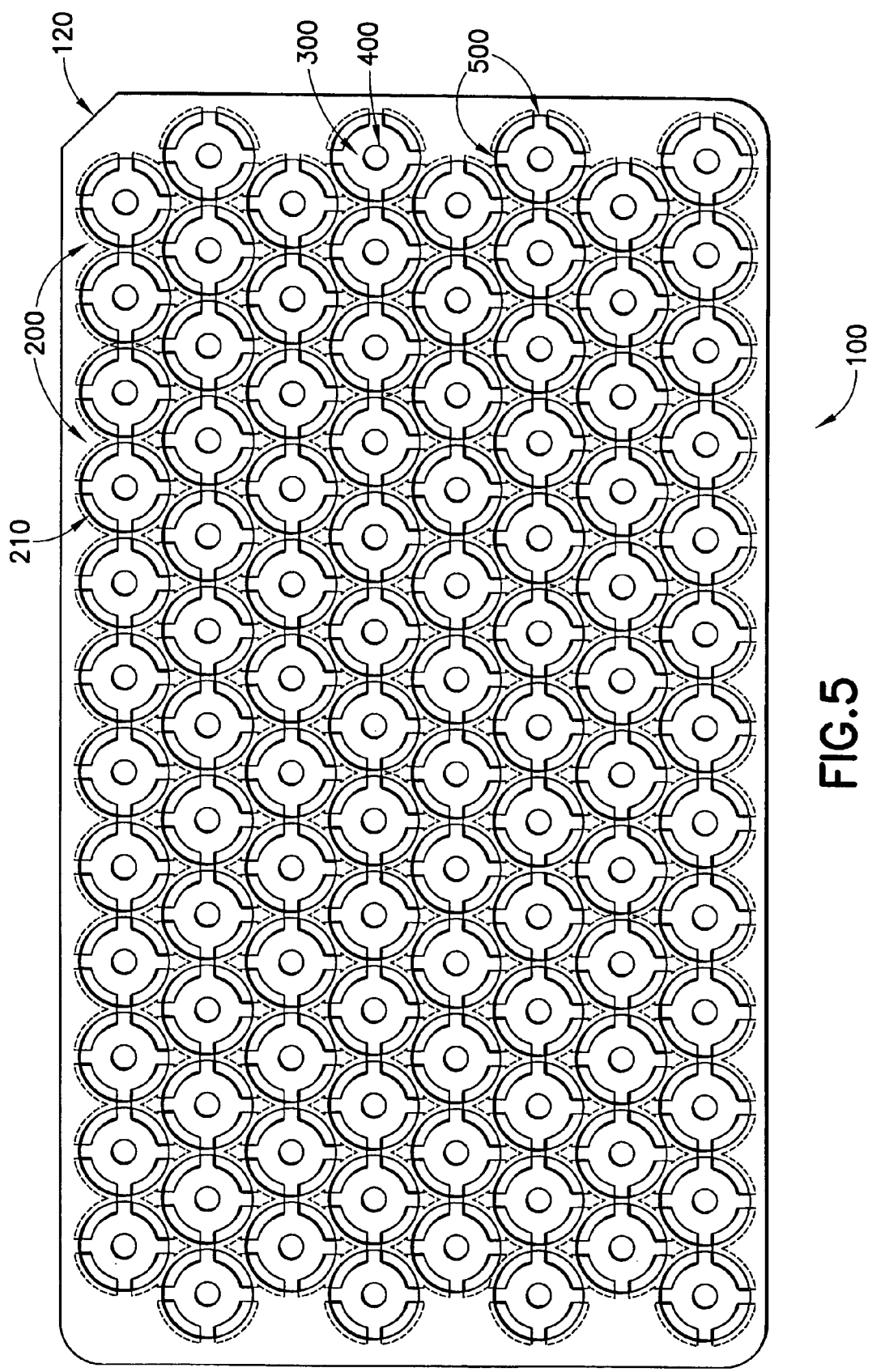
FIG. 5 is a top perspective view of a sample tube tray according to an embodiment of the present invention.

The preferred embodiments of the invention will now be described with reference to the attached drawing figures. FIG. 5 is an illustration of a preferred embodiment of the tray. The tray 100 is preferably made of nucleated polypropylene by injection molding, although other materials and processes may be used. The tray 100 has alternating rows of twelve wells and thirteen wells 200 for holding one hundred sample tubes (element 150 in FIG. 1) in a single tray. Each well has a bottom 300 supported by four legs 500, the legs 500 tapering inwardly from the well opening 210 to the bottom 300. To insure that liquids, moisture, steam and/or gases do not collect between the bottom of the well and the bottom of the tube, a hole 400 is formed in the center of the well bottom 300. Alternatively, the hole 400 could be replaced by a bump (not shown) that allows liquids, moisture, steam and/or gases to flow from between the well bottom and the bottom of the tube by minimizing the contact area between the well bottom and the bottom of the tube. The number of wells is dependent upon the size of the tubes and the invention is not limited by the examples shown in the Figures. In addition, the trays 100 may be used to hold and carry any type of suitable sample tube 150 regardless of the type of growth culture media or other substance, such as blood, may be in a sample tube 150.

Figure 6:
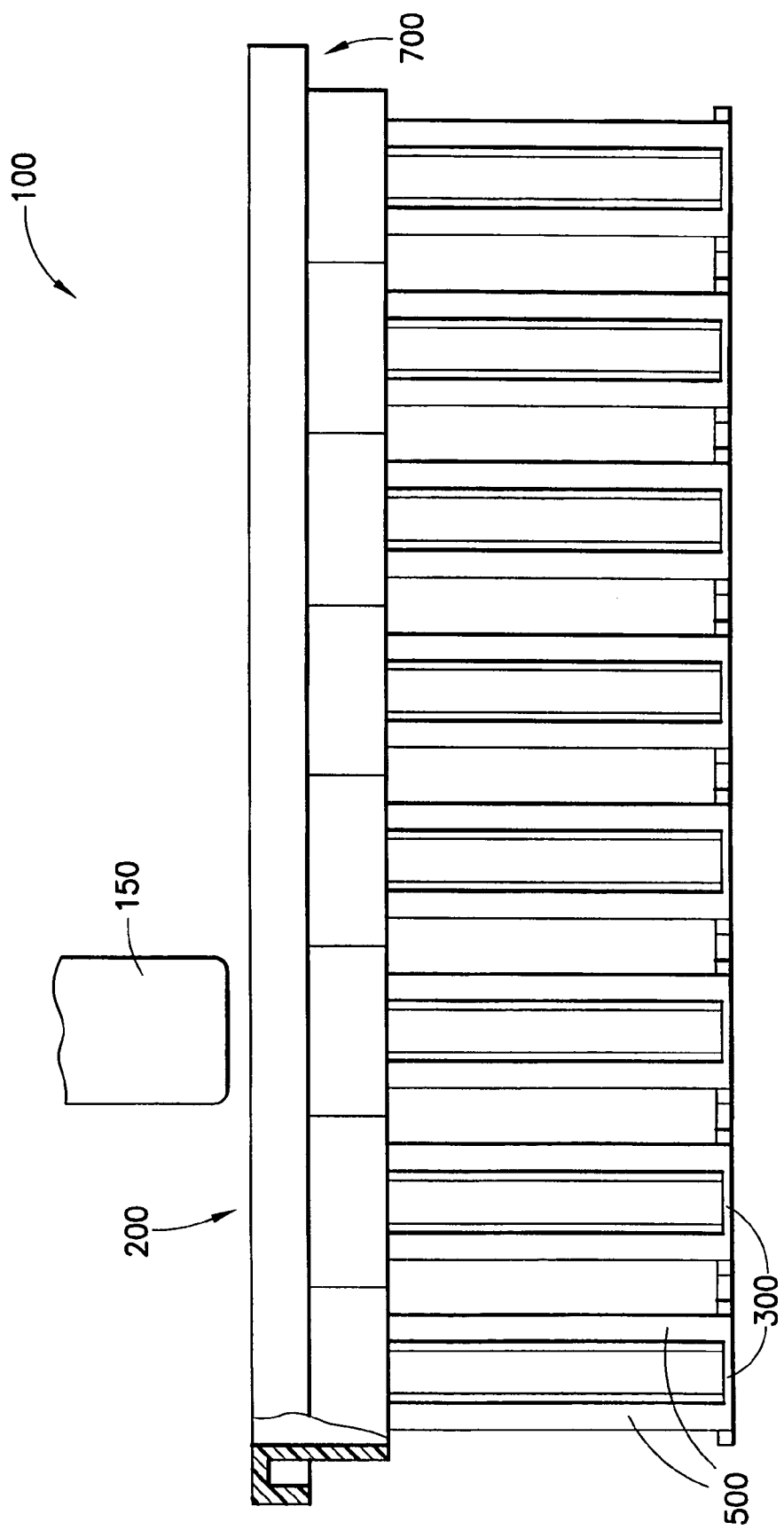
FIG. 6 is a side perspective view of a sample tube tray according to an embodiment of the present invention.

FIG. 6 is a side view of a preferred embodiment of tray 100. The alternating rows of twelve and thirteen wells 200 provide for a high well density. Legs 500 of the tray also have a support rib 600 that firmly hold the sample tubes in the tray. FIG. 6 also shows a flange 700 that prevents the trays from "shingling" sliding over one another when placed side by side in an autoclave or on the manufacturing line (e.g., a robotic tray loading station).

Figure 7:
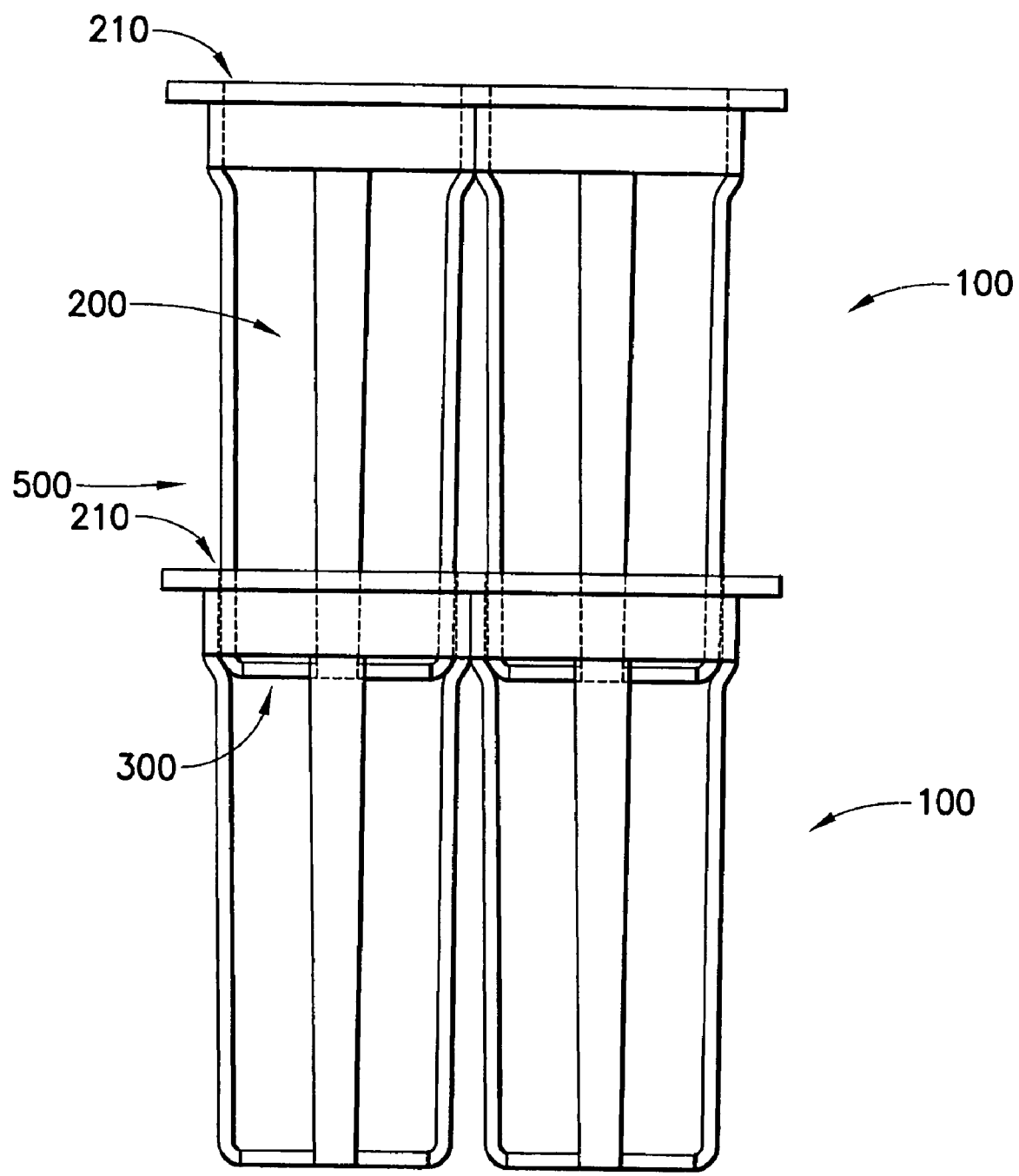
FIG. 7 shows the nesting feature of the sample tube trays in accordance with an embodiment of the present invention.

FIG. 7 shows an example of the nesting capability of a preferred embodiment of the tray 100. The trays 100 have a tapered leg 500 design that allows for nesting one tray into another. As can be seen in FIG. 7, the well bottom 300 of the well 200 is smaller in diameter than the well opening 210. This design feature provides greater stability when the trays are stacked, the ability to stack more trays together, and easier handling.

Figure 8:
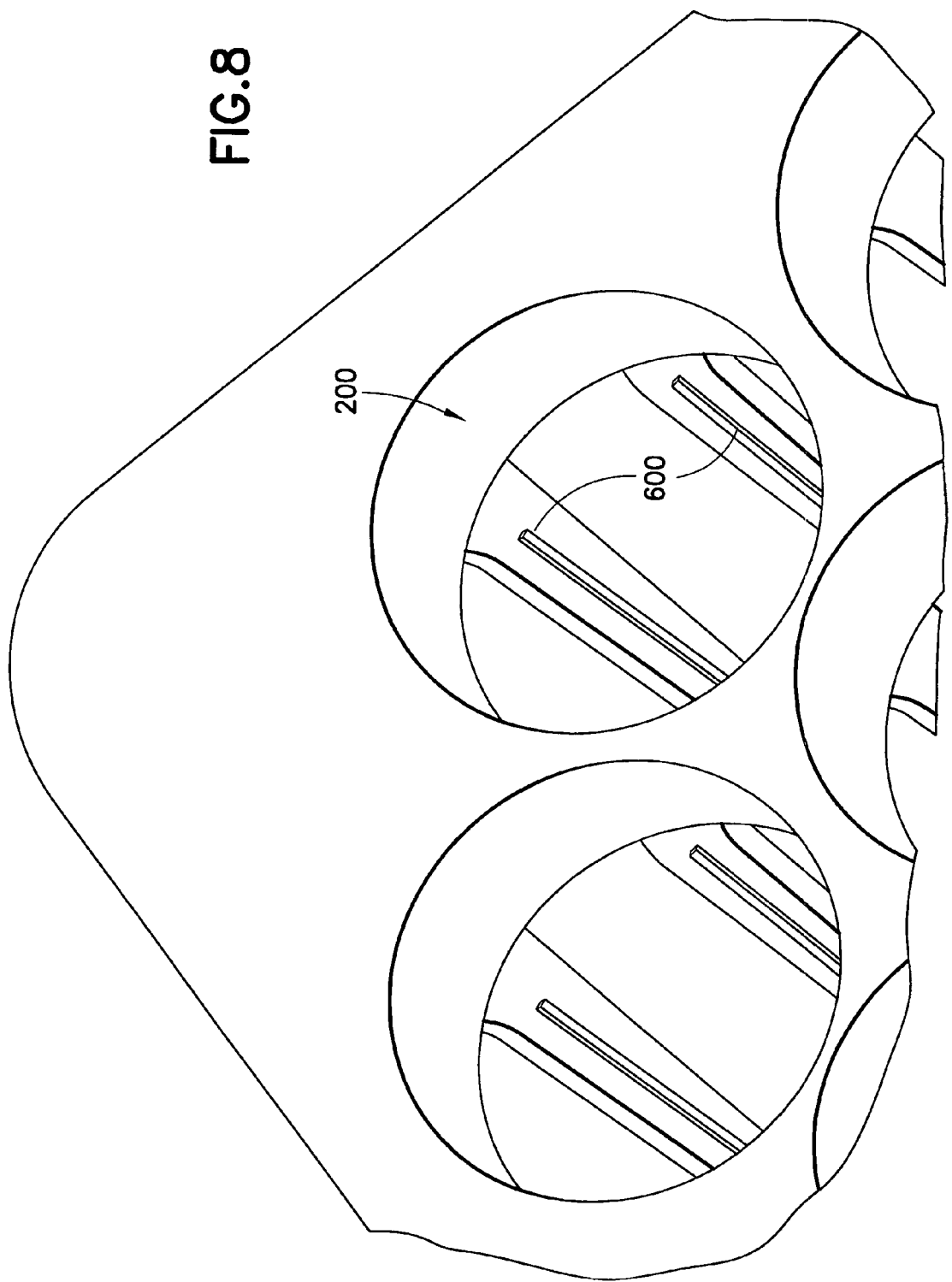
FIG. 8 shows a detail of the leg ribs inside the well of a sample tube tray according to an embodiment of the present invention.

FIG. 8 is a detailed view of the well 200 and leg support ribs 600. The leg support ribs 600 provide a firm frictional grip on the sample tubes when inserted into the tray. The support rib 600 also minimizes the cross-section of the leg that contacts the tube, thereby, allowing for moisture, liquid, steam and/or gas to flow around the tubes with minimal obstruction. The holes 400 in the well bottom 300 of the wells 200 allow any moisture, liquid, steam, and/or air to drain from beneath the sample tubes. Alternatively, the holes 400 may be replaced by bumps (not shown) that keep the bottom of the tube from making full contact with the well bottoms 300.

Figure 9:
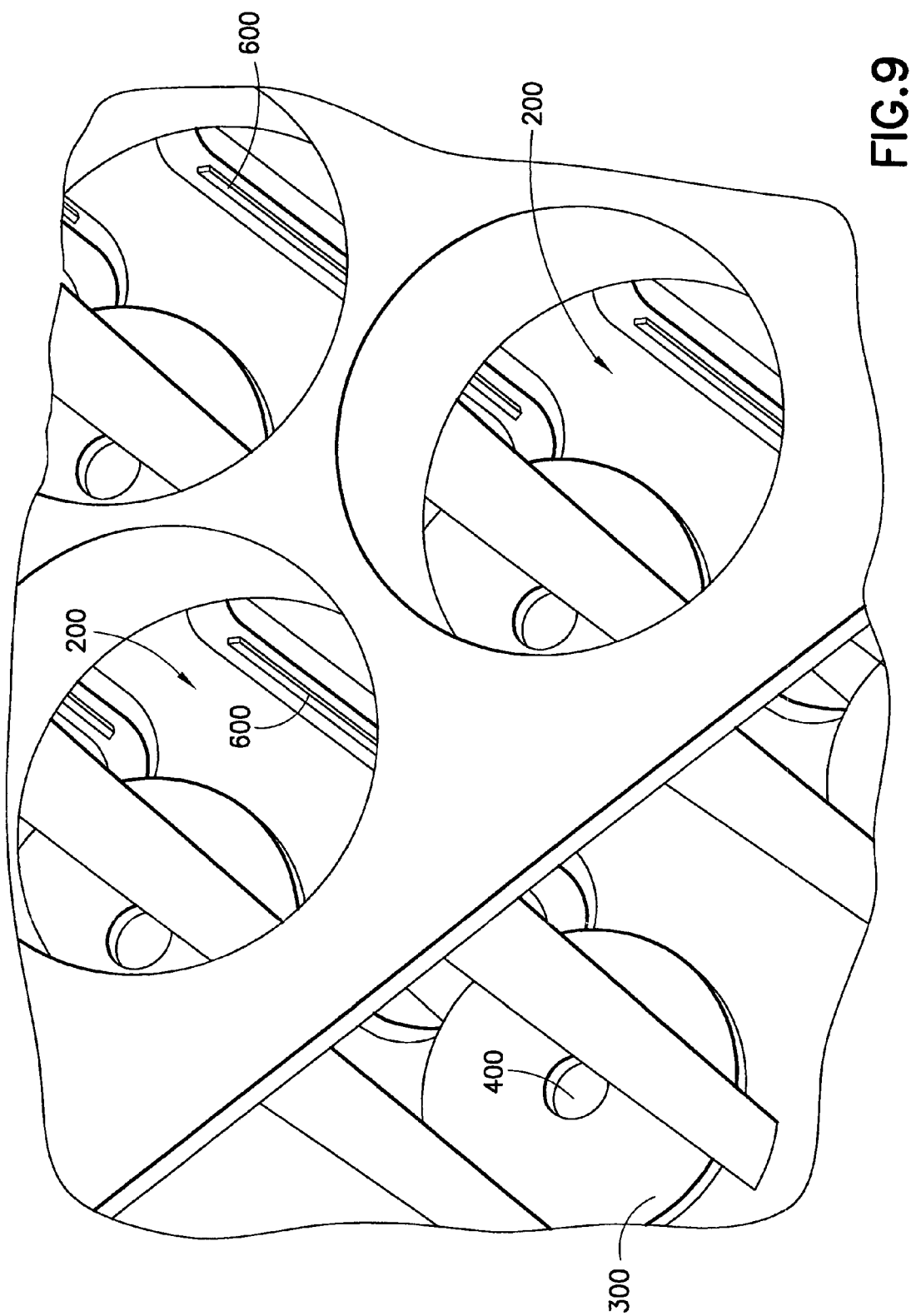
FIG. 9 is a detailed view of the leg ribs, well bottom, and bottom hole of a sample tube tray according to an embodiment of the present invention.

The openness of the sample tube well 200 design is best illustrated in FIG. 9. Only support ribs 600 of legs 500 and part of well bottom 300 (i.e., the part surrounding the hole 400) contact the sample tubes allowing steam and cooling air or water in the autoclave to surround most of the sample tube during the autoclaving and cooling processes. The sample tubes are heated and cooled more quickly when more of the surface area of the sample tube is subject to steam and cooling air or water. Conversely, enclosed cylindrical wells that completely contact the sample tube or the closed tray bottoms of the prior art metal trays substantially obstruct the flow of steam and air/water, thereby extending the heating and cooling processes.

Figure 10:
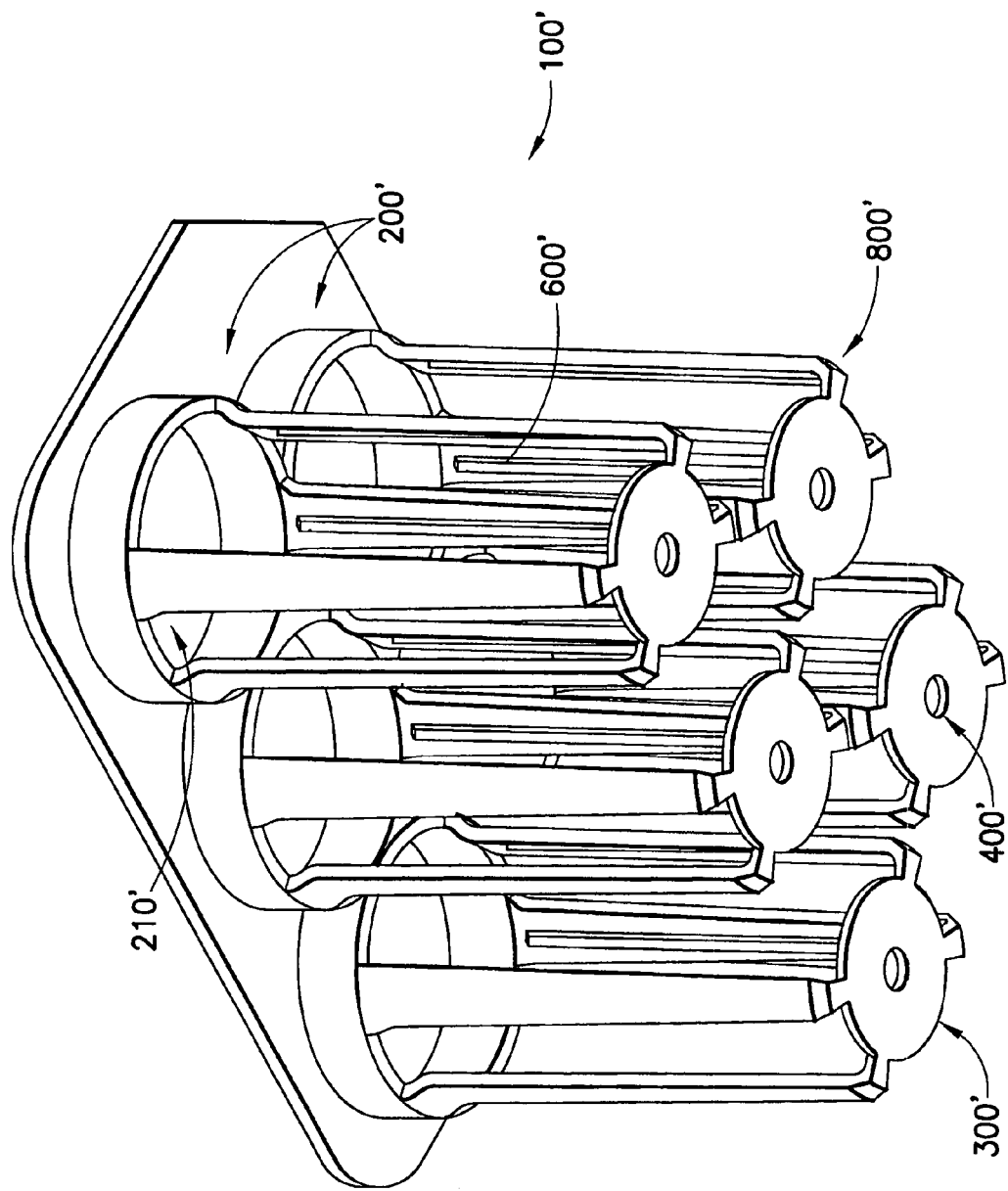
FIG. 10 shows an alternative configuration of the sample tube tray according to an embodiment of the present invention.

FIG. 10 is a view of an alternative embodiment of the present invention showing only five wells 200' in a tray 100'. The number and size of the wells 200' and well openings 210' are limited only by the requirements of the user. FIG. 10 provides a view from the underside of the tray 100' and shows the configuration of the bottom of the well 300', where the legs 500' attach to the bottom 300' by offsets 800'. The offsets 800' allow the bottom 300' to have the minimal amount of area contacting the sample tube, while still providing sufficient support. Additionally, the wells 200' have support ribs 600' to frictionally secure the sample tubes in the tray 100'. By minimizing the contact area between the tray 100' and the sample tubes, more surface area of the sample tube is exposed to the sterilizing steam or chemicals of the autoclave as well as the cooling gases or liquids. Any design that reduces areas where liquids and gases collect increases the overall efficiency of the heating and cooling cycles. Benefits of the minimized contact area include reduced time for the heating and cooling cycles, more uniform flow of liquids and gases around the sample tubes and through the tray, and less raw material used in the trays.

Since each sample tube in the tray 100 in the preferred embodiment (shown in FIG. 5) is supported by a well bottom 300, the trays 100 may be used in many ways in which the prior art shipping trays cannot be used by the customer or end user. The well bottoms 300 prevent the tubes from being pushed upward, which is a problem with the prior art shipping or packaging trays. This feature allows the free-standing trays 100 of the preferred embodiments of the present invention to be used in incubators, water baths, boilers, refrigerators, or at laboratory stations. Additional uses will occur to those skilled in the art.

The free-standing trays 100 are suitable to be used at a laboratory station to facilitate introducing microbial samples into the sample tubes 150, organizing the sample tubes 150 for the growth of the microbial samples, examining any microbial culture growth within the sample tubes 150 and collecting data corresponding to any microbial culture growth. The arrangement of the tray 100 also allows several sample tubes 150 to be organized in specific groupings according to patient, microbial, originating medical care provider, or by other typical groupings. Additionally, the design of the packaging tray 100 facilitates using the packaging tray 100 to grow the culture in a device, such as an incubator, that maintains the temperature of the culture and growth media at above room temperatures. Since the packaging tray 100 may be used to hold the sample tubes 150 in nearly all phases of the laboratory process, the end user can perform subsequent examination and data collection corresponding to the microbial growth. Additionally, the packaging trays may also be used to store the sample tube 150 in below-room-temperature devices, such as refrigerators or freezers, because the flat bottom design of the packaging tray 100 keeps the packaging tray 100 substantially level even on the uneven surfaces or gratings typically used in such devices.

Figure 11:
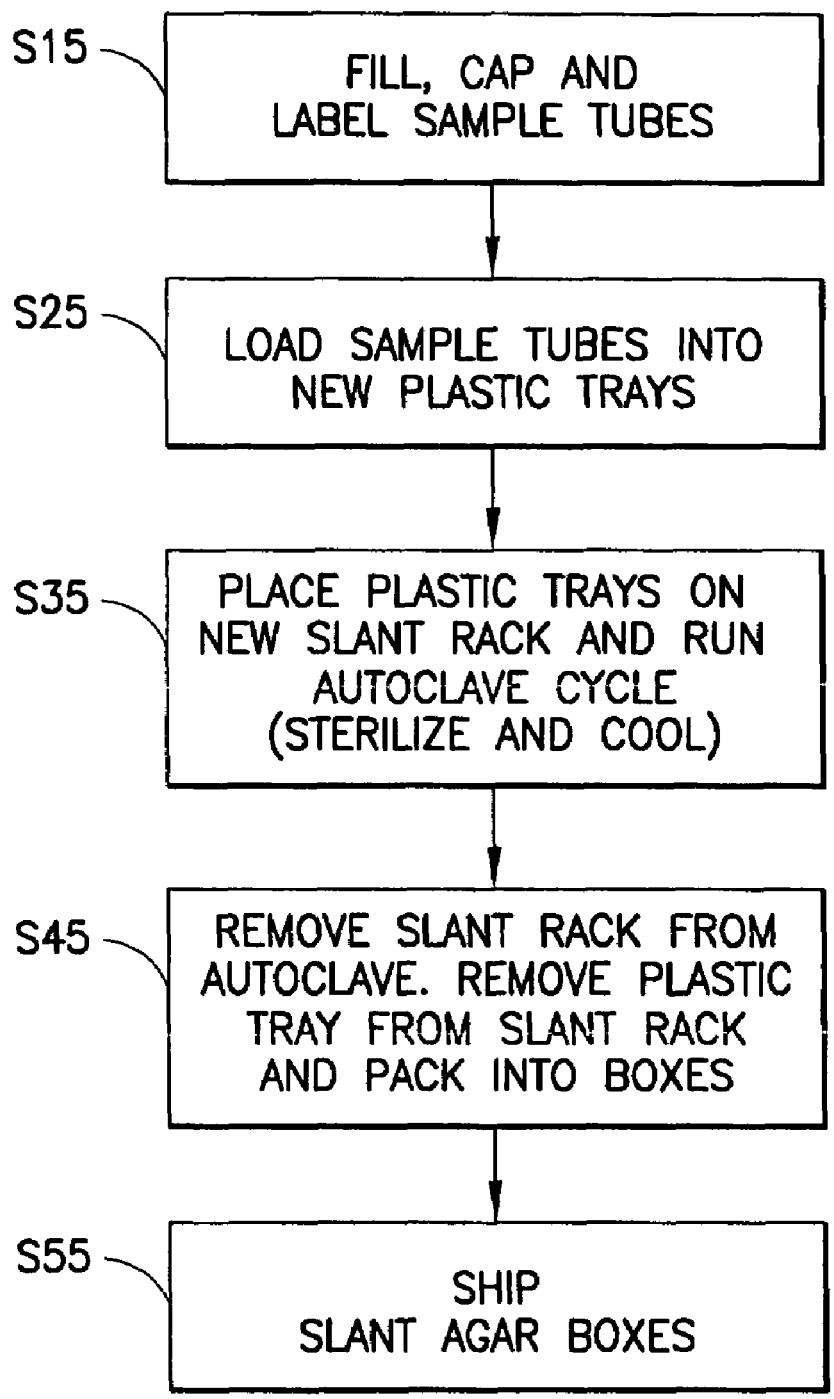
FIG. 11 is a flow chart of the process steps of an embodiment of the present invention.

A preferred embodiment of the inventive process using the new tray is shown in FIG. 11. The process begins with step S15 in which the sample tubes are filled, capped and labeled either manually or, preferably, automatically by a robotic device. The sample tubes have three different fill volumes to achieve the critical butt and slant measurements depending upon the culture growth medium and the size of the sample tube. The sample tubes will then be loaded into the new plastic trays in step S25, again, either manually or, preferably, automatically by a robotic device. Once the sample tubes have been loaded into the new trays, the trays and sample tubes are ready for an autoclave cycle in step S35.

The autoclave cycle in step S35 involves the use of a slant rack to hold the trays at a predetermined angle so that the butt and slant measurements meet the required specifications. The autoclave cycle includes a sterilization cycle that subjects the sample tubes and trays to a steam bath until either a parametric release cycle has been completed or until the sample tubes have been at a predetermined temperature for a predetermined amount of time. (Completion of the parametric release cycle is determined at a predetermined $F_o$ number that can be calculated by the formula shown at page 42 of the Getinge autoclave operators manual, Model GEV 7915 AR-1, the contents of which are incorporated herein by reference in their entirety. The autoclave is manufactured by Getinge Sterilization AB, 31044 Getinge, Sweden, which is an example of an appropriate autoclave.) After the sterilization cycle during which the temperature inside the autoclave reaches approximately 120 degrees Celsius, the autoclave evacuates the steam and begins lowering the temperature in the autoclave via heat exchangers. During this cooling phase, the agar solidifies at its predetermined slant. The temperature inside the autoclave can be raised beyond 120 degrees Celsius to evaluate the effects of the higher temperature on liquid products.

At step S45, the slant rack is then removed from the autoclave. From the slant rack, the trays of slant agar sample tubes are removed from the slant rack and placed in a shipping box. Finally, the slanted culture growth sample tubes are shipped to the customer in step S55. This process is much more streamlined than the prior art process with fewer opportunities for non-compliant slant agar product to be produced.

Figure 12A:
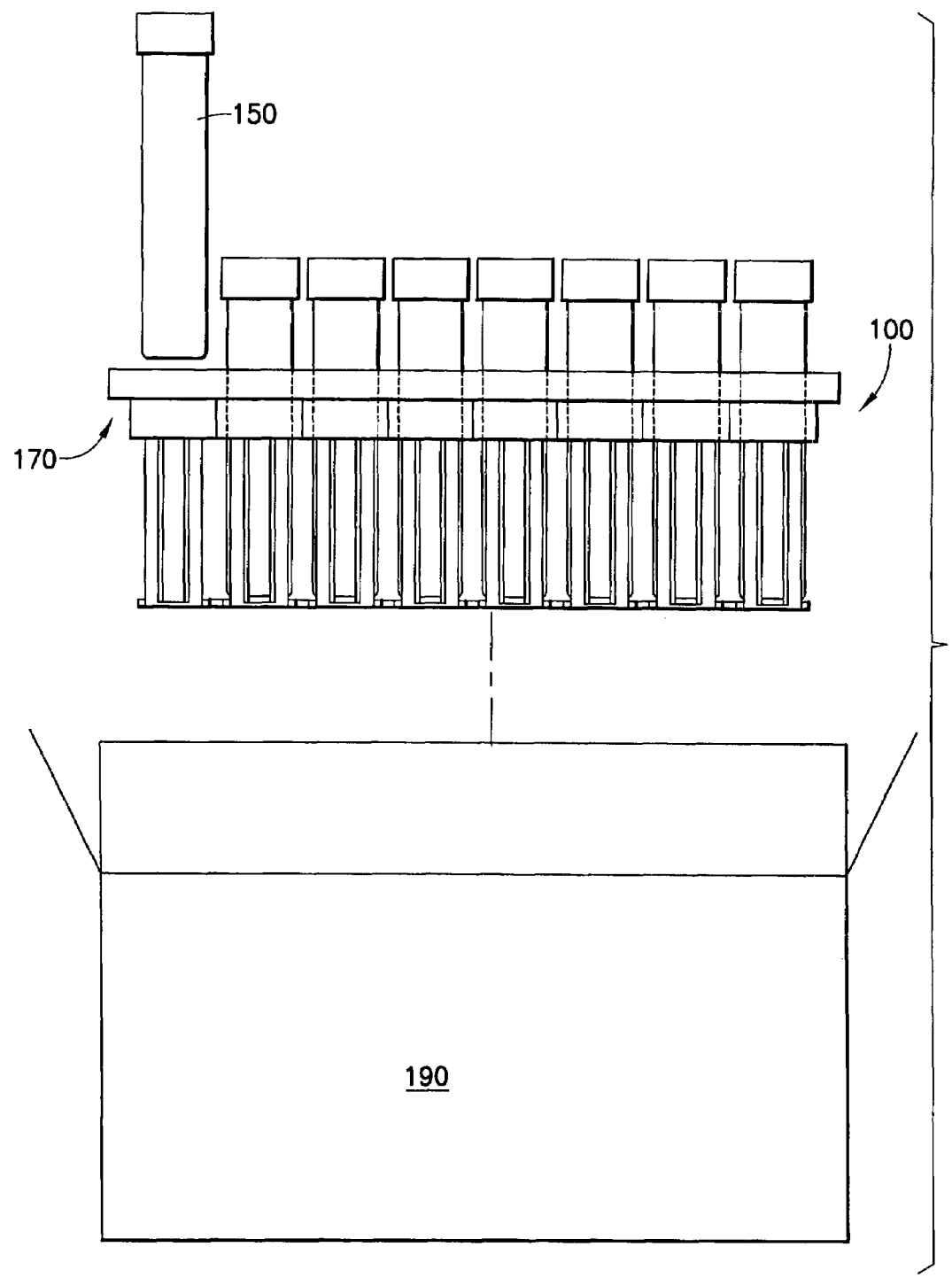
FIGS. 12A and 12B illustrates the manner in which a sampling tube tray according to an embodiment of the present invention can be placed in a shipping box.

Implementation of the process is facilitated by the use of the improved plastic autoclaveable trays 100. FIG. 12A illustrates the manner in which tubes 150 fill tray 100 which can then be placed in a shipping package 190. The trays 100, preferably made of nucleated polypropylene, are capable of withstanding high temperatures and pressures in the autoclave while securely holding the slanted sample tubes 150 in place. The nucleated polypropylene trays 100 may be made by injection molding; of course, other equivalent materials and processes may be used. The trays 100 are capable of being used from the beginning to the end of the growth culture medium production cycle. Essentially, once the filled, capped and labeled tubes 150 are placed in the tray 100, the individual sample tubes 150 need not be handled by a person or machine until delivered to the end user.

Figure 4:
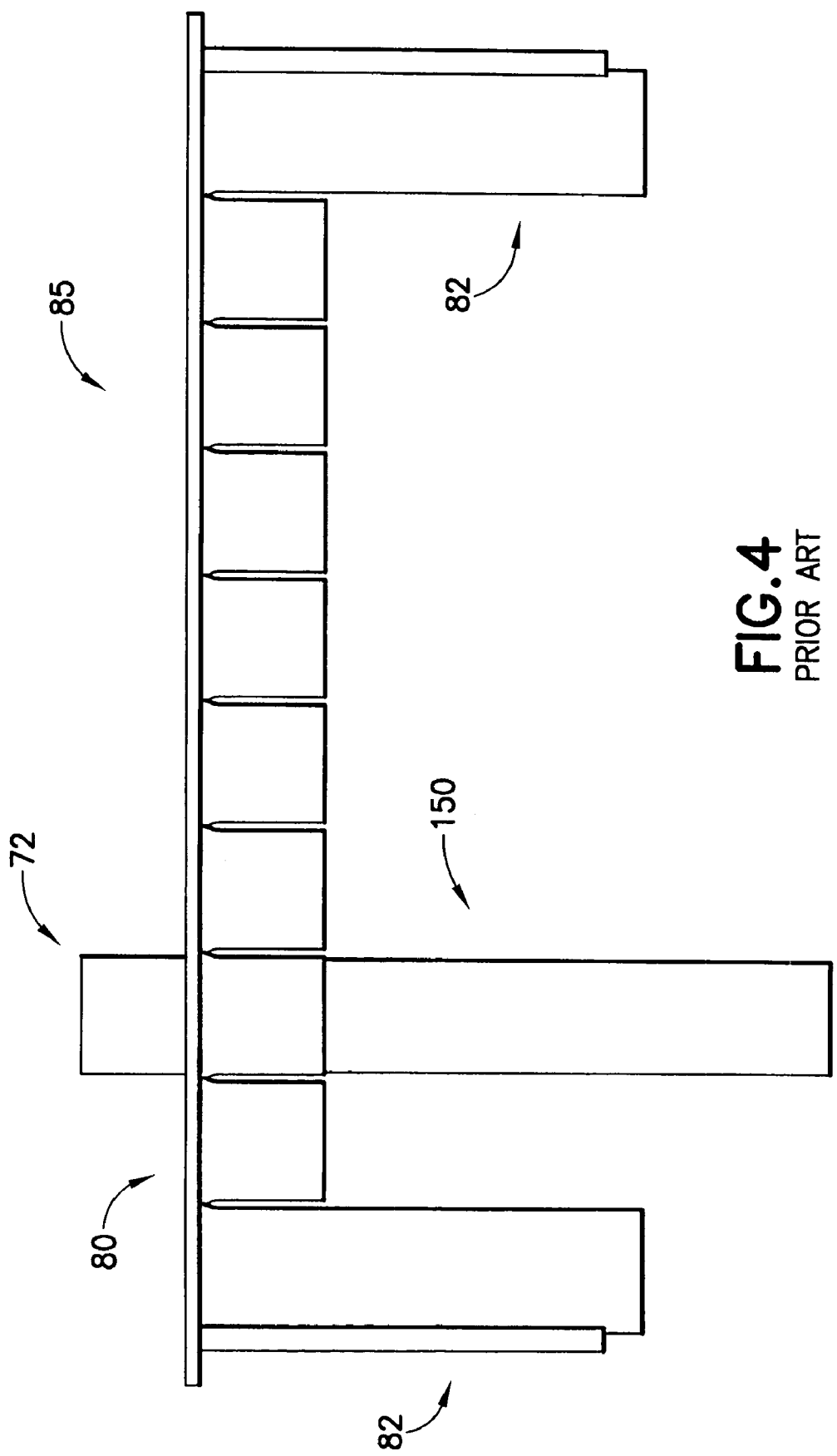
FIG. 4 illustrates a conventional shipping tray and exemplary sampling tube inserted therein.
Figure 12B:
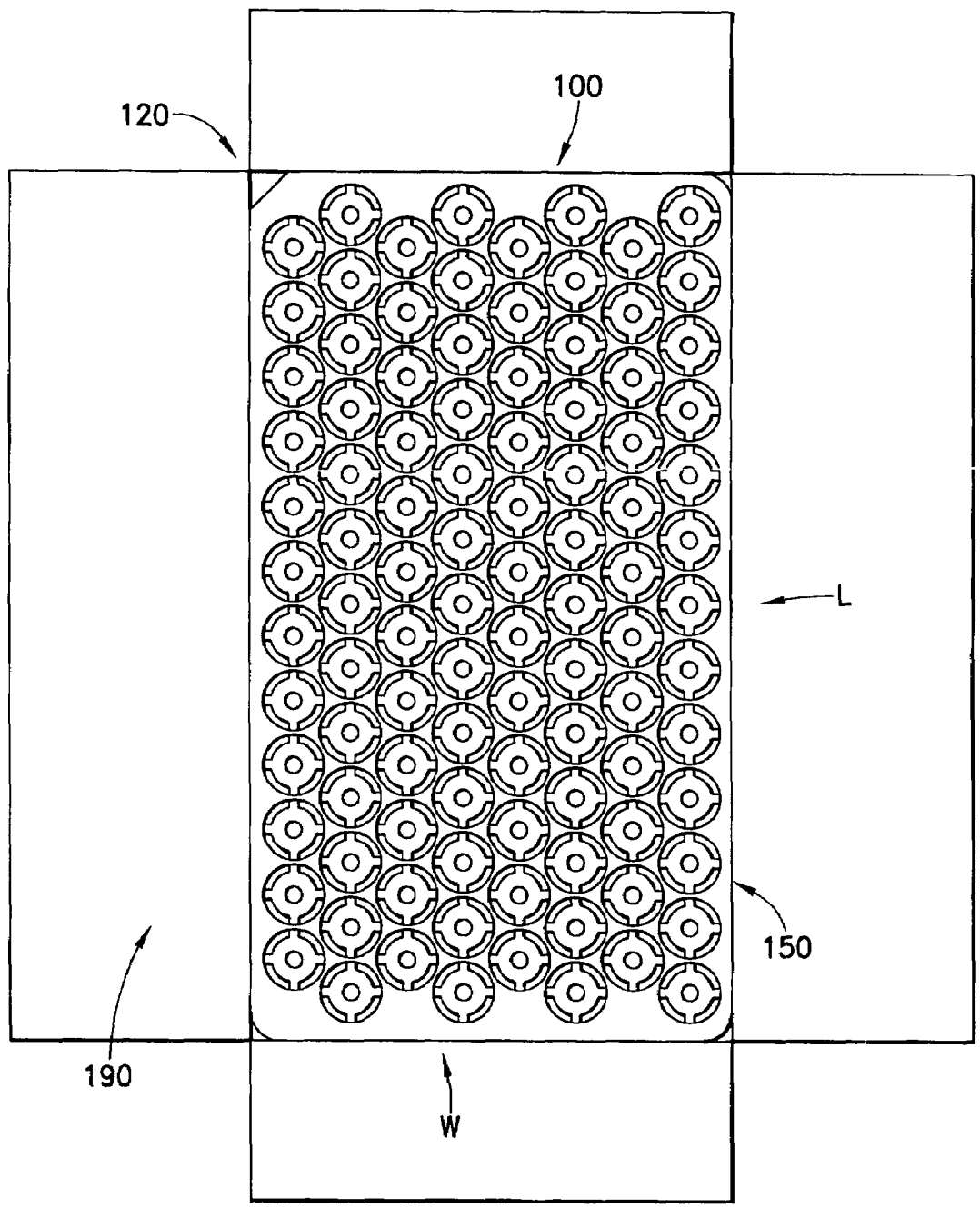

The preferred physical dimensions of the autoclaveable plastic tray 100 are different from those of prior art shipping trays. FIG. 12B shows the tray 100 with length L and width W not being equal, while the prior art tray (shown in FIG. 4) was typically a square tray with sides of equal dimensions.

Another feature of the new tray 100 is flange 170, which prevents the trays from "shingling" or sliding on top of one another when the trays are placed side by side. The flange 170 also serves to reinforce the edge of the tray which is securely held by the side support of the slant rack. As shown in FIG.

7B, the tray 100 has a notch 120 that can be used to orient the tray when placed in automatic filling machines. In addition, the notch 120 provides the end user with a place to grasp the tray when removing it from its shipping package 190. The tray 100 can be configured to hold one hundred sample tubes 150. As an example only, shipping package 190 is shown holding only one tray 100.

Figure 13:
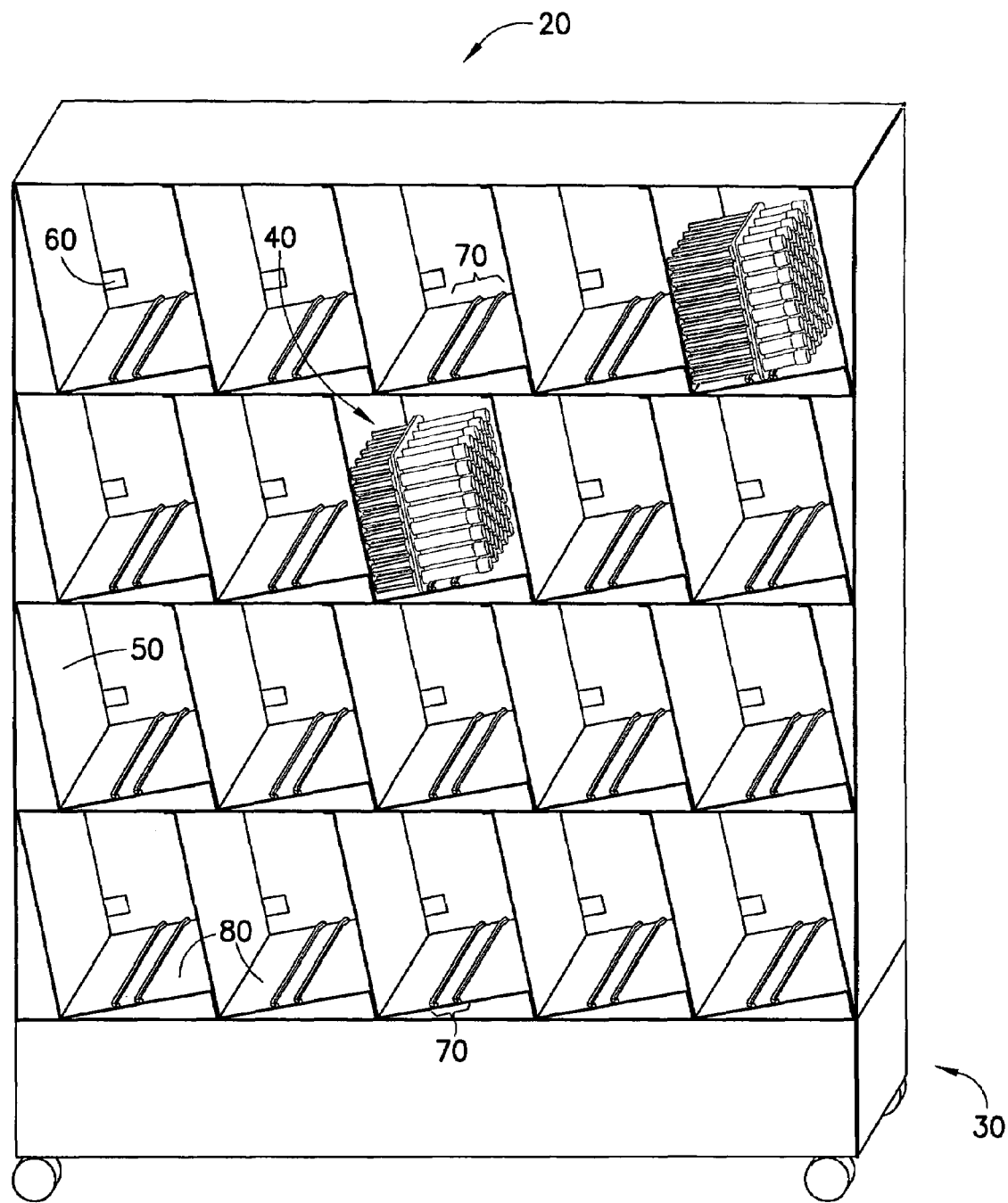
FIG. 13 illustrates a perspective view of the sampling tube trays loaded into a slant rack for placement into an autoclave according to an embodiment of the present invention.

In addition to the plastic autoclaveable tray, an improved slant rack is used to accommodate the new tray and for use in the new autoclave. FIG. 13 shows an example of a slant rack 20 being placed into an autoclave 10. The slant rack 20 rides on cart 30 until the cart 30 contacts the front of the autoclave 10. The slant rack is then pushed off of the cart 30 into the autoclave 10. Slant rack 20 is shown with only one tray 40 per shelf 80, but a preferred embodiment has two trays 40 per shelf. In the two tray 40 per shelf 80 embodiment, the side support 60 will be between the two trays 40.

Side support 60 is in the middle of the shelf 80 and trays 40 are loaded on each side of the slant rack 20. Side support 60 can be of any configuration so long as it supports the trays for at least half of the overall tray width (dimension W in FIG. 12B) to insure that the trays do not warp during the autoclave cycle. In addition, side support 60 may have at least one set of ribs (not shown) to securely hold trays made for 16 mm sample tubes as well as larger trays for 19 mm tubes. Shelf ribs 70 extend the length of the shelf 80 and provide further support for the trays.

Back support 50 is slanted at the predetermined angle to meet the slant agar product specification. Back support 50 and shelves 80 may be fabricated from perforated metal to insure minimal obstruction to the flow of liquids and gases through the trays and the slant rack 20 during an autoclave cycle (sterilization and cooling). Since the slant racks 20 are reused, the perforated metal must be of sufficient strength to handle the high temperature and pressure of the autoclave. The open area of the perforated metal is preferably 73.7 percent of the metal surface as a whole.

Figure 14:
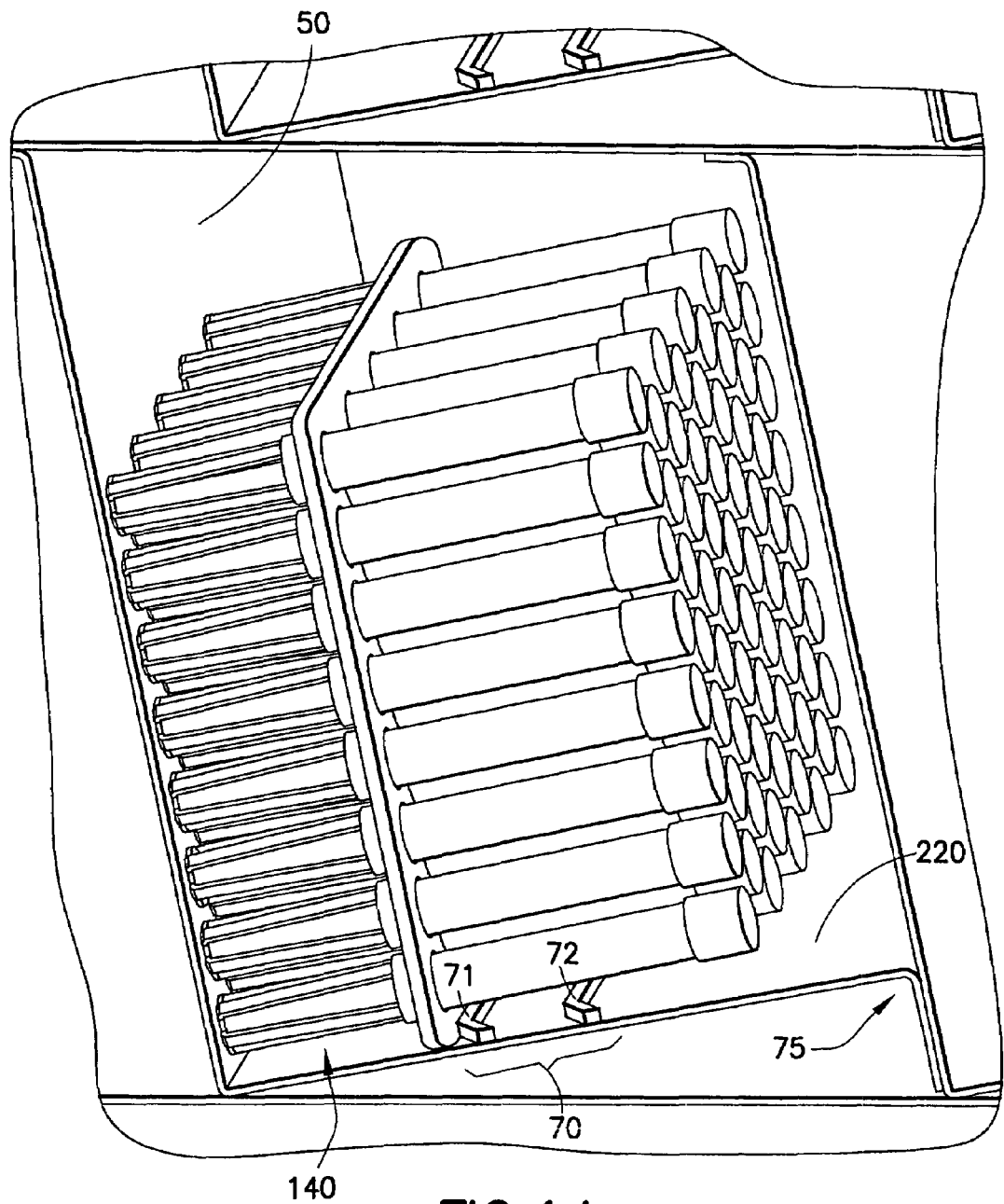
FIG. 14 is an example of sampling tube trays in a slant rack according to an embodiment of the present invention.

FIG. 14 is a detailed view of two of trays 250 in the shelf 220 of a slant rack. Shelf ribs 70 comprise two shelf ribs (71 and 72) spaced apart enough to accommodate two different tray 250 sizes. The 16 mm sample tubes use a smaller tray 200 than the 19 mm sample tubes. Therefore, the closest shelf rib 71 to the back support 50 supports the 16 mm tubes, while the shelf rib 72 further away from back support 50 supports the 19 mm sample tubes. The slant rack shelf 220 is wide enough to hold at least two trays 250. The preferred fixed slant angle for the shelves 220 in the slant rack is about 13.5 degree from horizontal based upon desired fill volumes to meet the applicable product specifications. Shelf corner 75 can also have any configuration that insures that the shelves will be adequately supported at the about 13.5 degree slant angle. Although, when manufacturing either broth or non-slanted agar products the slant angle would be zero degrees from horizontal.

Figure 15:
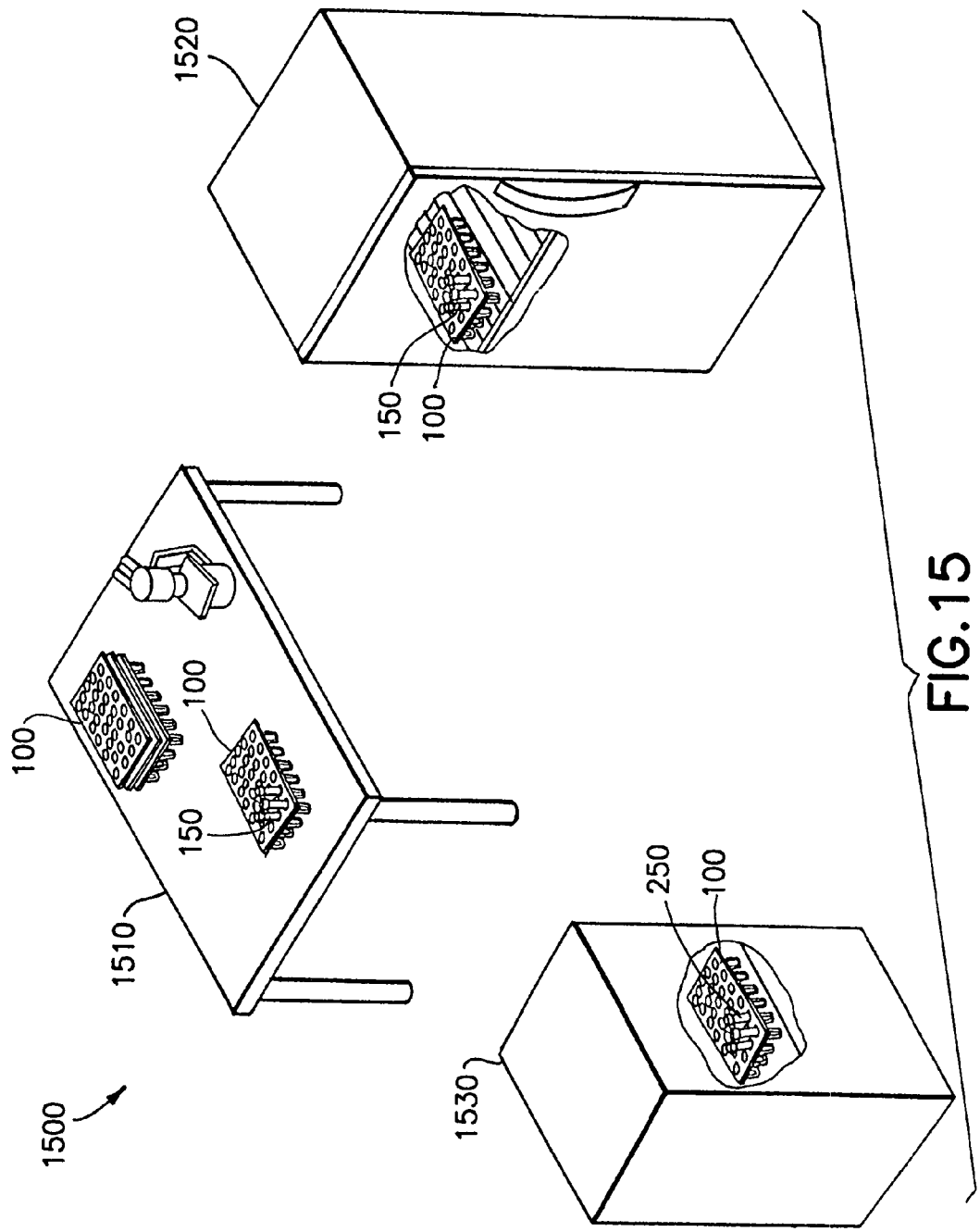
FIG. 15 is a perspective view of embodiments of the present invention as used in a laboratory environment.

FIG. 15 is a perspective view of an exemplary laboratory 1500. The exemplary laboratory 1500 is shown with a laboratory station 1510 and a sample tube tray 100 with sample tubes 150 being prepared for analysis. In addition, refrigerator 1520 and incubator 1530 are shown with several sample tube trays 100 stored therein while awaiting for further analysis or other usage such as storage or preparation of microbial samples.

While the invention herein disclosed has been described by means of specific embodiments and applications thereof, numerous modifications and variations can be made thereto by those skilled in the art without departing from the scope of the invention as set forth in the claims.

What is claimed is:

1. A method for processing microbial cultures comprising:
    loading a plurality of sample tubes filled with culture media into at least one tray;
    placing said at least one tray onto a rack, said rack maintaining said at least one tray and the sample tubes within that tray in a position wherein the culture media slants at a slant angle within said tubes wherein the slant angle is measured from the sample tubes in a horizontal position;
    sterilizing said tray holding said plurality of tubes filled with culture media in a sterilizing apparatus;
    cooling said rack and tray holding said plurality of tubes filled with culture media and said rack after completion of the sterilizing step, so that the culture media solidify within said tubes at said slant angle; and
    transferring said tray holding said plurality of tubes after the cooling step from said rack into shipping packages for shipment, wherein said tray is ready for use by an end user.

2. The method of claim 1, wherein said plurality of sample tubes have been pre-filled with culture media, capped and labeled prior to sterilization.

3. The method of claim 1, wherein the rack maintains said at least one tray in a position that slants the culture media at said slant angle within said tubes by using a side support and a bottom shelf support ridge.

4. The method of claim 1, wherein the sterilization step is performed by an autoclave or by an inspissator.

5. The method of claim 4, further comprising the step of placing said rack into an autoclave or an inspissator.

6. The method of claim 1, wherein said tray provides sufficient space around each tube to allow for substantially unobstructed flow of liquids, moisture, steam and/or gas around the tube.

7. The method of claim 1, further comprising the step of using said tray at a laboratory station for at least one of placing microbial samples in said sample tubes, organizing said sample tubes for growth of said microbial samples, or collecting data corresponding to said microbial samples.

8. The method of claim 7, wherein said tray is stored in a below-room temperature environment.

9. The method of claim 7, wherein said tray is stored in an above-room temperature environment.

10. The method of claim 1, further comprising the step of using said tray at a laboratory station to facilitate examining microbial culture growth within said sample tubes and collecting data corresponding to said microbial culture growth.

11. The method of claim 1, wherein the cooling step is performed within the same apparatus that performs the sterilizing step.

12. The method of claim 1, wherein the slant angle is non-zero.

13. A method of growing microbial cultures using a sample tube tray comprising the steps of:
    preparing slanted growth culture media in sample tubes disposed in a tray including sterilizing said tray containing said sample tubes with slanted growth culture media followed by cooling said tray thereby solidifying said slanted growth culture media;
    transferring said tray containing said sample tubes with slanted growth culture media after cooling into a shipping container, wherein said tray is ready for use by an end user;
    removing said tray containing said sample tubes with slanted growth culture media from said shipping container by said end user;

holding said sample tubes in said tray at a laboratory station while placing microbial samples in said sample tubes; and processing said sample tubes to grow microbial cultures.

14. The method of claim 13, wherein said processing step comprises storing said sample tubes and trays in a refrigerator.

15. The method of claim 13, wherein said processing step comprises storing said sample tubes and trays in an incubator.

16. A method of growing microbial cultures using a sample tube tray comprising the steps of:

preparing growth culture media including holding said sample tray in a position that maintains culture media disposed within said sample tubes in a non-slanted horizontal position and sterilizing said tray containing said sample tubes with growth culture media followed by cooling said tray thereby solidifying the horizontal, non-slanted growth culture media;

transferring said tray containing said sample tubes with growth culture media after cooling into a shipping container, wherein said tray is ready for use by an end user;

removing said tray containing said sample tubes with growth culture media from said shipping container by said end user;

holding said sample tubes in said tray at a laboratory station while placing microbial samples in said sample tubes; and processing said sample tubes to grow microbial cultures.

17. The method of claim 16, wherein said processing step comprises storing said sample tubes and trays in a refrigerator.

18. The method of claim 16, wherein said processing step comprises storing said sample tubes and trays inan incubator.

19. A method for processing microbial cultures comprising:

loading a plurality of sample tubes filled with culture media into at least one tray;

placing said at least one tray onto a rack, said rack maintaining the sample tubes within said tray in a substantially horizontal position wherein the culture media within said sample tubes is non-slanted;

sterilizing said tray holding said plurality of tubes filled with culture media in a sterilizing apparatus;

cooling said rack and tray holding said plurality of tubes filled with culture media and said rack after completion of the sterilizing step, so that the culture media solidify within said tubes at said slant angle; and transferring said tray holding said plurality of tubes after the cooling step from said rack into shipping packages for shipment, wherein said tray is ready for use by an end user.

* * * * *